(12) United States Patent
Abolfathi et al.

(10) Patent No.: US 7,354,270 B2
(45) Date of Patent: Apr. 8, 2008

(54) SURGICAL DENTAL APPLIANCE

(75) Inventors: Amir Abolfathi, Menlo Park, CA (US); Loc X. Phan, San Jose, CA (US); Peter Knopp, Palo Alto, CA (US)

(73) Assignee: Align Technology, Inc., Santa Clara, CA (US)

( * ) Notice: Subject to any disclaimer, the term of this patent is extended or adjusted under 35 U.S.C. 154(b) by 126 days.

(21) Appl. No.: 10/744,458

(22) Filed: Dec. 22, 2003

(65) Prior Publication Data

US 2005/0136371 A1 Jun. 23, 2005

(51) Int. Cl.
*A61C 5/00* (2006.01)
*A61C 3/00* (2006.01)

(52) U.S. Cl. .............. 433/215; 433/6; 606/105

(58) Field of Classification Search ......... 433/215, 433/6, 18; 606/105; 602/17, 902, 5; 128/848, 128/859–862
See application file for complete search history.

(56) References Cited

U.S. PATENT DOCUMENTS

| | | | | |
|---|---|---|---|---|
| 1,797,480 A | * | 3/1931 | Preston ..................... | 602/5 |
| 2,502,902 A | * | 4/1950 | Tofflemire ................ | 606/54 |
| 3,348,311 A | * | 10/1967 | Weissman ................. | 433/18 |
| 3,675,327 A | * | 7/1972 | Huget et al. ............. | 433/215 |
| 4,073,061 A | * | 2/1978 | Bergersen ................. | 433/6 |
| 4,090,299 A | * | 5/1978 | Williams .................. | 433/18 |
| 4,202,328 A | * | 5/1980 | Sukkarie ................... | 433/18 |
| 4,391,589 A | | 7/1983 | Monfredo et al. | |
| 4,505,672 A | * | 3/1985 | Kurz ........................ | 433/6 |
| 4,644,941 A | | 2/1987 | Ogle, II | |
| 4,813,406 A | | 3/1989 | Ogle, II | |
| 5,037,638 A | * | 8/1991 | Hamer et al. ............. | 424/52 |
| 5,184,955 A | | 2/1993 | Baer et al. | |
| 5,281,135 A | | 1/1994 | Schwestka-Polly | |
| 5,499,633 A | * | 3/1996 | Fenton ..................... | 128/848 |
| 5,794,627 A | * | 8/1998 | Frantz et al. ............ | 128/848 |
| 5,941,247 A | * | 8/1999 | Keane ...................... | 128/848 |
| 5,975,893 A | | 11/1999 | Chishti et al. | |
| 6,055,986 A | * | 5/2000 | Meade ...................... | 128/848 |
| 6,086,365 A | * | 7/2000 | Fields ...................... | 433/18 |
| 6,170,485 B1 | * | 1/2001 | Orrico ...................... | 128/848 |
| 6,210,162 B1 | | 4/2001 | Chishti et al. | |
| 6,217,325 B1 | | 4/2001 | Chishti et al. | |
| 6,227,850 B1 | | 5/2001 | Chishti et al. | |
| 6,227,851 B1 | | 5/2001 | Chishti et al. | |
| 6,299,440 B1 | | 10/2001 | Phan et al. | |
| 6,309,215 B1 | | 10/2001 | Phan et al. | |
| 6,315,553 B1 | * | 11/2001 | Sachdeva et al. ......... | 433/24 |
| 6,318,994 B1 | | 11/2001 | Chishti et al. | |
| 6,332,775 B1 | | 12/2001 | Gordils Wallis | |
| 6,347,940 B1 | | 2/2002 | Gordils Wallis | |
| 6,371,761 B1 | | 4/2002 | Cheang et al. | |
| 6,386,864 B1 | | 5/2002 | Kuo | |
| 6,386,878 B1 | | 5/2002 | Pavlovskaia et al. | |
| 6,390,812 B1 | | 5/2002 | Chishti et al. | |
| 6,394,801 B2 | | 5/2002 | Chishti et al. | |
| 6,398,548 B1 | | 6/2002 | Muhammad et al. | |
| 6,406,292 B1 | | 6/2002 | Chishti et al. | |
| 6,409,504 B1 | | 6/2002 | Jones et al. | |
| 6,450,807 B1 | | 9/2002 | Chishti et al. | |
| 6,454,565 B2 | | 9/2002 | Phan et al. | |

(Continued)

*Primary Examiner*—John J Wilson

(57) ABSTRACT

A dental splint includes upper and lower appliances having cavities shaped to receive teeth on a patient's maxillary and mandibular arches, respectively; and a connection member adapted to fixedly secure the upper and lower appliances together.

27 Claims, 2 Drawing Sheets

U.S. PATENT DOCUMENTS

| | | |
|---|---|---|
| 6,457,972 B1 | 10/2002 | Chishti et al. |
| 6,458,162 B1 | 10/2002 | Koblish et al. |
| 6,463,344 B1 | 10/2002 | Pavloskaia et al. |
| 6,471,511 B1 | 10/2002 | Chishti et al. |
| 6,485,298 B2 | 11/2002 | Chishti et al. |
| 6,488,499 B1 | 12/2002 | Miller |
| 6,497,574 B1 | 12/2002 | Miller et al. |
| 6,499,997 B2 | 12/2002 | Chishti et al. |
| 6,702,575 B2 * | 3/2004 | Hilliard ............... 433/6 |
| 6,726,478 B1 * | 4/2004 | Isiderio et al. ........ 433/69 |
| 6,767,208 B2 * | 7/2004 | Kaza ................... 433/24 |
| 2002/0150859 A1 * | 10/2002 | Imgrund et al. ....... 433/24 |
| 2003/0065259 A1 | 4/2003 | Gateno et al. |
| 2003/0138473 A1 | 7/2003 | Koblish et al. |
| 2003/0211441 A1 | 11/2003 | Mauro |

* cited by examiner

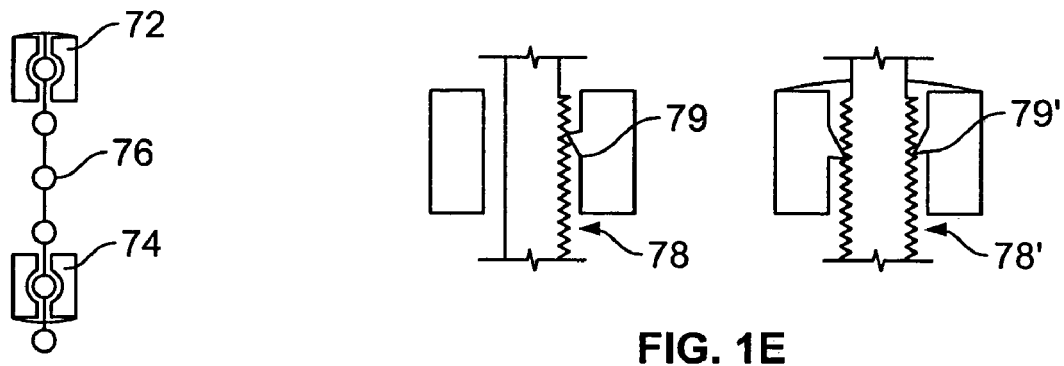
FIG. 1D
FIG. 1E
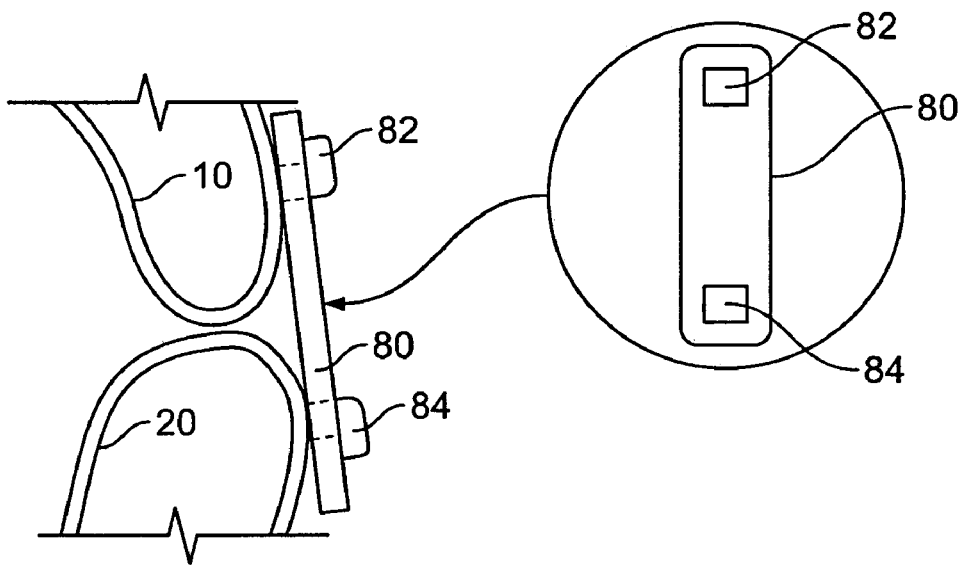
FIG. 1F
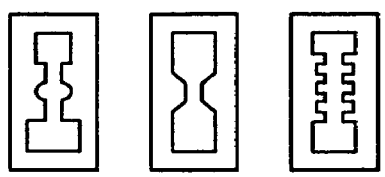
FIG. 1G
FIG. 1H

SURGICAL DENTAL APPLIANCE

BACKGROUND OF THE INVENTION

Some people need surgery to correct maxilla to mandible relationship for better occlusion. Surgery may be required because the bite relationship is so severe that it is beyond the ability of conventional orthodontia. During such treatment, the bones are repositioned and splints are used in order to bring about temporary intramandibular, intramaxillary or intermaxillary fixations in jaw surgery. During surgery, one or both jaws are cut free from neighboring bone and tissue. The surgeon brings the dental arches into the desired occlusion and fixes the jaw(s) in the new relative position(s). Steps are then taken to secure the jaw(s) to the bone and tissue again. To help maintain the intended occlusion as healing occurs, the jaws are connected to each other using a splint.

As discussed in U.S. Pat. No. 5,184,955 to Baer, et al., a dislocated and repositioned tooth is connected to its neighboring teeth by means of a metal wire which, after an etching pretreatment, is fixed to the front surface of the teeth by means of composite material. For the long-term after-treatment of gnathoorthopedic cases, it is known to stick rigid, metal holding elements, so-called brackets, onto the tooth surface. All these holding elements are connected to one another by means of a metal wire which is loosely guided through them. By means of tensioning and, if necessary, periodically retensioning of the wire, adjustive tensioning forces are transmitted via the holding elements, which in this case have the function of transmitting forces, to the teeth to be treated. This method also can only be applied by the dentist who is familiar with it; moreover, the rigidity of the holding elements renders their exact positioning more difficult.

Additionally, as noted in Baer, et al., it has also already been attempted to produce a dental splint with synthetic material only, is to say without a wire-shaped connecting link. This method could not be implemented, however as it is difficult to shape the synthetic material exactly and, on the other hand, it often does not withstand the forces which arise in the area of the teeth, and the removal of the synthetic material has also proved difficult. As the composite material must be removed again after a certain time, it is important that from the outset an amount which is as small as possible be used if this material is applied, in other words that the adhesion surface is delimited as exactly as possible, whereas on the other hand, however, the wire-shaped connecting link is nevertheless to be securely surrounded by composite at the respective fastening point and the formation of hollow points, in particular between wire and teeth surface, must be avoided.

Additionally, the patient's bite relationship has to be correct. Presently, the surgeon sets the bite of the patient manually using plaster study models and then creating a template of the occlusion which he later will use as a guide during surgery. In surgery, the surgeon resets the jaw bone and then establishes the approximate bite relationship using the guide that he had fabricated early manually using study models. This present method of fabricating the guide template and manually setting the bite using study models is time consuming, inaccurate and cumbersome.

SUMMARY OF THE INVENTION

A dental splint includes upper and lower appliances having cavities shaped to receive teeth on a patient's maxillary and mandibular arches, respectively; and a connection member adapted to fixedly secure the upper and lower appliances together.

Advantages of the invention may include one or more of the following. The system provides a dental appliance for the temporary passive splinting of teeth. The system fixes the relative positions of the two arches and allows for mounting or positioning the inter arch-relationship during surgery using the appliances. The system allows the doctor to plan the desired treatment on a computer.

The system also provides the ability to quickly remove the appliance when needed. For example, if a complication occurs during the surgery and the doctor needs to remove the appliance, a zipper-like tearing mechanism is provided to the doctor so that the doctor can pull on a tab and cut the appliance apart. The removal capability is important during surgery if the doctor has already separated the jaw from the facial structure and the jaw is only connected by tissue.

The surgeon can send the dental records and impressions of the patient to an appliance fabricator. The fabricator can digitally set bite relationship and fabricate appliances with index points which allow the surgeon to easily re-establish bite relationship during surgery with the appliances inserted into the patient's teeth.

The setting of the occlusion is benefited by the incorporation into the splint of a means of indexing several opposing points on the arches. These points are guides to mitigate or eliminate uncertainty in the relative positions. The design of the appliance index points may be in any configurations that will allow easy bite setting and bite recreation for the surgeon. The appliance material may have physical properties for precise fitting over the teeth of the patient and should also be easily removable due to the post surgical fragile state of the patient. The appliance material may have environmental switching properties for changing physical properties for easy removal and insertion purposes. The appliance material may have the ability to carry active ingredients and release it in a controlled fashion. The active ingredients may be fluoride and/or any therapeutic compounds. The appliance material may be transparent or having tooth matching color.

BRIEF DESCRIPTION OF THE DRAWINGS

FIG. 1D illustrates a fourth embodiment of the present invention.

FIG. 1E illustrates a fifth embodiment of the present invention.

FIG. 1F illustrates a sixth embodiment of the present invention.

FIG. 1G illustrates a seventh embodiment of the present invention.

FIG. 1H illustrates an eighth embodiment of the present invention.

DESCRIPTION OF THE SPECIFIC EMBODIMENTS

Figure 1A:
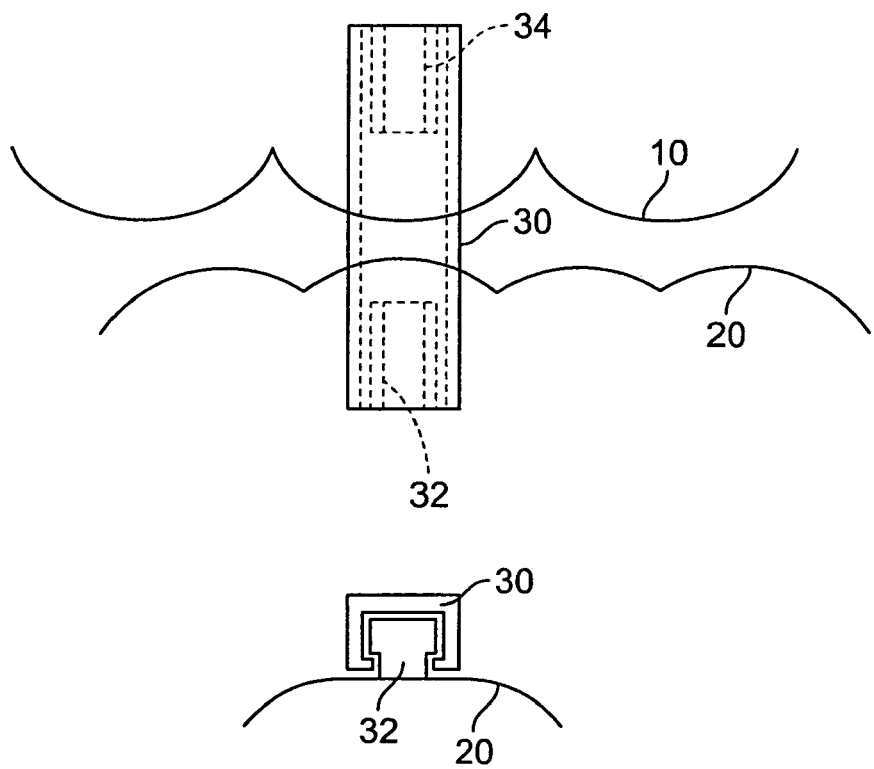
FIG. 1A illustrates a first embodiment of the present invention.

Referring now to FIG. 1A, one surgical appliance embodiment is disclosed. The appliances 10 and 20 fix the patient's maxillary (upper) and mandibular (lower) teeth to one another temporarily with regard to the healing of a jaw. The appliances 10 and 20 can be polymeric shells having cavit(ies) shaped to receive and resiliently position teeth. The polymeric shells will preferably, but not necessarily, fit over teeth in the upper or lower jaw. Often, only certain one(s) of the teeth will be positioned while other teeth provide a base or anchor region for holding the repositioning appliance in place as the resilient positioning force is applied against the tooth or teeth to be repositioned. In complex cases, however, many or most of the teeth can be repositioned at some point during the treatment. In such cases, the teeth which are moved can also serve as a base or anchor region for holding the repositioning appliance. Additionally, the gums and/or the palette can serve as an anchor region, thus allowing all or nearly all of the teeth to be positioned simultaneously.

The polymeric appliance 10 or 20 can be formed from a thin sheet of a suitable polymeric, such as Tru-Tain 0.03 in. thermal forming dental material, Tru-Tain Plastics, Rochester, Minn. 55902. Usually, no wires or other means will be provided for holding the appliance in place over the teeth. In some cases, however, it will be desirable or necessary to provide individual anchors on teeth with corresponding receptacles or apertures in the appliance 10 so that the appliance can apply an upward force on the tooth which would not be possible in the absence of such an anchor. The appliances 10 and 20 immobilize the maxilla and mandibular during a healing period. Specific methods for producing the appliances 10 and 20 are described hereinafter.

In FIG. 1A, for the mutual, intermaxillary connection of the two jaws, one or more connection members 30 hold the appliances 10 and 20 in a predetermined three dimensional relationship that provides a proper bite occlusion for the patient during healing.

In the embodiment of FIG. 1A, the connection members 30 include two T-shaped attachments 32 and 34, also known as the lower and upper portions respectively, positioned on the appliances 10 and 20. A connection member 30 is slidably positioned on the attachments 32 and 34 to secure the appliance 10 to the appliance 20. In FIG. 1A, the connection member 30 is a C-shaped channel that engages the T-shaped attachments. Alternates to the connection member 30 include bands strips, or cords that bind the two appliances 10 and 20 together. Additionally, the connection members 30 can be, for example, metal, C-shaped, plastically deformable clips, self-fixing plastic loops or wire ligatures.

In one embodiment, the attachments 32 and 34 have non-round shapes to prevent slippage or side-to-side shifts between the appliances 10 and 20. The non-round shapes can be square, rectangular, triangular, among others.

In another embodiment, the connection member 30 and attachments 32 and 34 have ratchets, barbs, hooks, or other appropriate geometry on at least one side. One end of each connecting component 32, 34 or 30 is larger in one or more dimensions to stop the component from passing through the holes or slots in one arch's appliance through which the element passes. The appliance for the opposing arch also has pass through holes or slots in the attachments. Each attachment 32 or 34 on the appliance 10 or 20 engages the connection member 30, band or strip or cord such that the connection member 30, band or strip can pass in only one direction—withdrawal is stopped by elements in the component that correspond to the ratchets, barbs, or hooks on the connecting component.

In one embodiment, the connection members 30 are placed in two or more positions on one of the appliances worn on the patient's dental arches. These positions may overlay one or more teeth. For example, they are not restricted to any locus by the natural geometry and composition of the dental arches. In another embodiment, complimentary connection members are placed on the opposing arch directly under (or above depending on which arch received the initial placements) the connection member 30. The mesiodistal alignment of the upper and lower attachments need not be perfect. The fixation method allows for some latitude of location. The buccolingual and occlusogingival positions may be adjusted to accommodate an individual's occlusion and dentition as well as to facilitate the manufacturing processes.

In one embodiment, a series of perforations are formed on the body of the appliances using a laser beam or a mechanical punch, among others. A tab is attached to one end of the appliance. The tab can be pulled by the doctor to separate the appliance into portions so that it can be quickly removed when needed. For example, if a complication occurs during the surgery and the doctor needs to remove the appliance, a zipper-like tearing mechanism is provided to the doctor so that the doctor can pull on a tab and cut the appliance apart. The removal capability is important during surgery if the doctor has already separated the jaw from the facial structure and the jaw is only connected by tissue.

Figure 1B:
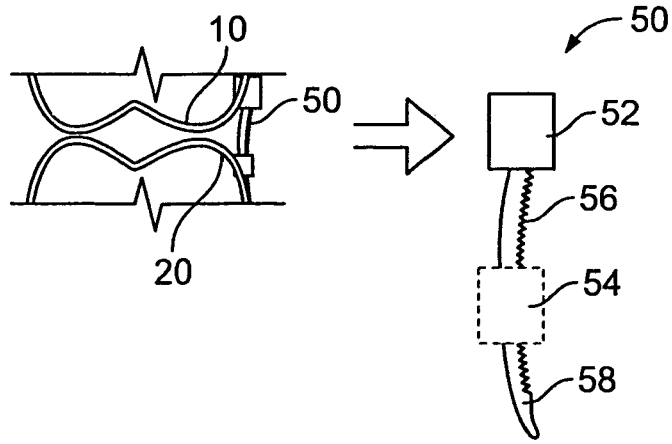
FIG. 1B illustrates a second embodiment of the present invention.

FIG. 1B shows a second embodiment of a connection member 50. In this embodiment, the connection member 50 includes an upper portion 52 affixed to the upper appliance 10 and a ratcheted portion 56. The upper and ratcheted portion 52 and 56 are one piece in one embodiment. A lower portion 54 is affixed to the lower appliance 20 and is a separate element. A section of 50 projects beyond the portion 54, and pulling on this section 58 brings the upper and lower appliances 10 and 20 (and by extension, upper and lower jaws) closer together and more firmly or solidly fixes their positions relative to each other.

Other similar embodiments include but are not limited to a ladder connection member (FIG. 1C), a bead connection member (FIG. 1D), and a pawl/ratchet connection member (FIG. 1E).

Figure 1C:
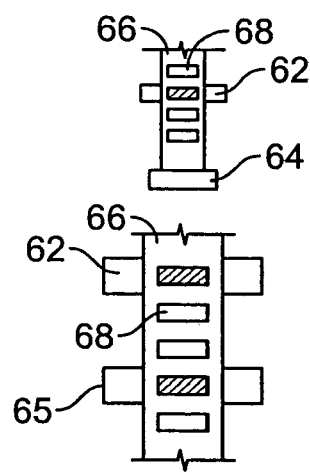
FIG. 1C illustrates a third embodiment of the present invention.

In FIG. 1C, an upper portion 62 is a separate element. The upper portion 62 has a base which is mounted on one of the appliances 10 or 20 and an extended portion which projects from the appliance. A ladder 66 has a plurality of openings 68 between ladder steps. The ladder 66 is fixedly secured to a lower portion 64. The lower portion 64 and the ladder 66 is attached to the remaining appliance. One of the openings on the ladder 66 then is snapped onto the extended portion to secure the ladder 66 to the upper portion 62.

Although the embodiment discussed above is a two-piece system, a three piece embodiment can be used with separate upper portion 62, ladder 66 and lower portion 65.

FIG. 1D shows yet another embodiment where an upper portion 72 has a base which is mounted on one of the appliances. The upper portion 72 has a curvaceous center portion adapted to receive a bead on a bead string 76. A second bead on the bead string 76 is snappably secured to the center of a lower portion 74. The upper and lower portions 72 and 74 provide openings where the bead string 76 can be fit into the portions 72-74. By repositioning the bead string 76, the upper and lower appliances (and by extension, upper and lower jaws) are brought closer together and more firmly or solidly fixes their positions relative to each other.

The embodiment in FIG. 1E shows a pawl and ratchet relationship between the connection member and the attachments fixed on the appliances. By pulling on the ratchet, the upper and lower appliances (and by extension, upper and lower jaws) are moved closer together and more firmly or solidly fixes their positions relative to each other. Pawls 79 and 79' interact with ratchets 78 and 78' to move the appliances. Other embodiments alternate ratchet locations and designs having the indicated upper and lower elements switch locations.

FIG. 1F shows a third embodiment where the inter-arch fixation component is a rectilinear hasp 80 that snaps onto or over hook elements 82 and 84 to prevent relative motion between the upper and lower arches. The hook line elements also have a mainly rectilinear profile in the buccolingual direction. Rather, they are for engaging elastics when the hasps are removed. The hook elements are bonded to or embedded in the aligners.

The approximately intimate contact between the parallel sides of the hasp holes and the hooks prevents lateral shifting of the aligners relative to each other because the hasp holes cannot rotate about the hook elements. When a sufficient number (for example three or more) of these assemblies are placed on the dental arch form, the upper and lower arches cannot shift.

All other possible motion will be prescribed as well. When desired, the hasps may be easily removed by cutting them in one or more places. Various design iterations such as those shown in FIGS. 1G and 1H permit a press or snap fit onto the hook elements while still allowing for easy removal. In one embodiment, the material is preferably clear or translucent, and the thickness is anticipated to be approximately one millimeter. The facial dimensions are expected to be similar to those of the teeth or smaller.

The hook element is also preferably fabricated from clear or translucent material. The dimensions are determined by those of the hasp. Various hook element designs are possible. The prominence and curvature of the hook will be determined by factors such as mechanical requirements, elastic material used, patient comfort, aesthetics, and manufacturability.

During use, the surgeon captures and sends dental records and impressions of the patient to an appliance fabricator such as the assignee of the instant invention or a suitable dental laboratory for fabricating the appliances. The fabricator scans the dental records and digitizes the dental impressions. The fabricator then digitally sets a proposed bite relationship, and the digital file is sent to the doctor. The doctor can visualize the interarch relationship using a virtual articulator. The doctor can reposition the arches to specify the desired spatial position for the teeth. The information is sent back to the fabricator to build a physical model of the patient's teeth (using SLA technology, for example) and subsequently build the appliances. The fabricator makes the appliances with index points which allow the surgeon to quickly re-establish bite relationship during surgery with the appliances inserted into the patient's teeth. The design of the index points may be in any configurations that will allow easy bite setting and bite recreation for the surgeon.

In one embodiment, the bite-setting of the teeth may be aligned automatically. In this embodiment, the models of the jaws are moved so that they are aligned to the features of one or more corresponding teeth. The features may be based on cusps, fossae, ridges, distance-based metrics, or shape-based metrics. Shape-based metrics may be expressed as a function of the patient's arches, among others. For example, cusp features associated with each tooth may be used. Cusps are pointed projections on the chewing surface of a tooth. In a detection stage, a possible cusp is viewed as an "island" on the surface of the tooth, with the candidate cusp at the highest point on the island. "Highest" is measured with respect to the coordinate system of the model, but could just as easily be measured with respect to the local coordinate system of each tooth.

The set of all possible cusps is determined by looking for all local maxima on the tooth model that are within a specified distance of the top of the bounding box of the model. First, the highest point on the model is designated as the first candidate cusp. A plane is passed through this point, perpendicular to the direction along which the height of a point is measured. The plane is then lowered by a small predetermined distance along the Z axis. Next, all vertices connected to the tooth and which are above the plane and on some connected component are associated with the candidate cusp as cusps. This step is also referred to as a flood fill step. From each candidate cusp point, outward flooding is performed, marking each vertex on the model visited in this matter as part of the corresponding candidate cusp. After the flood fill step is complete, every vertex on the model is examined. Any vertex that is above the plane and has not been visited by one of the flood fills is added to the list of candidate cusps. These steps are repeated until the plane is traveled a specified distance. After the detection stage, the cusp detection process may include a rejection stage where local geometries around each of the cusp candidates are analyzed to determine if they possess non-cusp-like features. Cusp candidates that exhibit non-cusp-like features are removed from the list of cusp candidates. Various criteria may be used to identify non-cusp-like features. According to one test, the local curvature of the surface around the cusp candidate is used to determine whether the candidate possesses non-cusp-like features. Alternatively, a measure of smoothness is computed based on the average normal in an area around the candidate cusp. If the average normal deviates from the normal at the cusp by more than a specified amount, the candidate cusp is rejected.

Additionally, a simplified set of movement physics (kinematics) may be applied to the bite-set dental models. The process can perform a simulation using a simplified set of interacting forces on the jaws in relation to one another. The simplified physical simulation allows the system to focus on motions involving much contact between the jaws. The physical simulation allows the system to render realistic physically correct jaw movements when the jaws come into contact with each other. A range of simulated motion may be supplied using a library of motions. One typical motion supplied by the library is a protrusive motion where the lower jaw is moved forward and backward to bring the front teeth on both jaws into contact with each other. Another motion is a lateral motion found in food chewing. The lateral motion involves moving the jaws side to side. Other motions that may be supplied in the library include motions that are "tooth guided" where the path of the lower jaw is guided by the teeth in contact with each other. Next, the process adjusts the final position based on contacts observed during the simulation of motions. The result of the simulation is analyzed, the position of each tooth can be adjusted if contacts associated with that tooth are deemed excessive. Finally, based on the contact data generated, the process determines whether additional motion simulations need to be done. The motion simulation may be rerun until the contacts associated with each tooth are acceptable to the treating orthodontist. The tooth model manipulation process can be done subjectively, i.e., the user may simply reposition teeth in an aesthetically and/or therapeutically desired manner based on observations of the final position or based on the simulation of contacts. Alternatively, rules and algorithms may be used to assist the user in repositioning the teeth based on the contacts.

In one embodiment called Automated Bite Setting Using PVS Bites, PVS bites are digitally scanned using a template to evaluate bite set results. When the technician is ready to set the bite, he or she will bring up all three objects (upper arch, lower arch and the PVS bite) on the screen. A technician runs the bite set software, and compares the digital bite against the impressions on the PVS bite. In other words, the PVS bite, in conjunction with patient photos, will be used as a reference to approve the digital image of the bite. If the correct occlusion cannot be determined digitally, detailed plasters are poured up and the bite is manually registered. The cases can be checked against photos supplied by the submitting doctor and any adjustments required to the digital bites are then performed.

In another embodiment called Automated Bite Setting with Centric Occlusion, a process implemented in software attempts to find a "best fit" between digital models of the upper and lower arches, much like fitting two plaster models together. This process works well for most cases, with the exception of open bites since a best fit position cannot be ascertained for these cases. The centric occlusion auto bite setting process consists of two main steps:

1. Initial setting of the upper jaw;
2. Finding of best bite, starting from initial position 1).

To find initial position the following process is used:

1. For every molar and premolar in the upper jaw corresponding tooth in the lower jaw is found. Teeth with no pair are not used in finding initial position;
2. Transform minimizing sum of squared distances between corresponding teeth is found and applied to the upper jaw;
3. The upper jaw is shifted in positive Z direction to be above the lower one;
4. To find bite a physical model is used.

In this model G force is applied to the upper jaw. In case of collision repulsion force occurs between jaws. This force is proportional to square of collision. The position of the upper jaw is calculated from equation of solid body motion. When the final position of the upper jaw is achieved, the stability of this position is tested. For this purpose force in side directions is applied to the jaw. If jaw moves easily then position is judged to be unstable and series of bite setting process from new initial positions is initiated. For example, new initial positions are shifted from the original one in Y direction from −8 mm to +7 mm with the step of 3 mm. In this way 7 different bite positions are determined including the first one. The user is then asked to select an optimal position.

If the software could not find a proper position for the upper jaw, it will show the following dialog to let user select between different iterations. In this dialog, a user can hide upper jaw and turn the collisions on, to see which position is most proper. When user presses any button, the upper jaw is set to the selected position and the scene is left open for correction and saving.

The above embodiments take the quesswork out of bite setting and eliminate the need to pour plaster models for bite issues. For example:

1. If a good PVS bite and good photos are submitted, the jaws are aligned or adjusted to the PVS bite. The resulting model is confirmed (and adjusted as necessary) based on photos of the patient's bite.
2. If a good PVS bite is submitted without photos or with poor photos, bite will be set based on the PVS bite. The same applies to the scenario of no PVS bites but good photos.
3. If no PVS bites or good photos are submitted, bite is set assuming a centric occlusion and by allowing the software to determine a best fit solution, much like fitting two plasers together.
4. If for some reason, the technician is not confident of the resultant digital bite, plaster models are poured to confirm the bite. This scenario assumes a doubtful digital bite set and lack of good photos. Just like the third scenario, this will assume a centric occlusion.

Once the virtual models of the teeth are bite-set, virtual attachments are placed on the virtual models of the teeth. To illustrate, for the embodiment of FIG. 1A, two T-shaped virtual attachments are positioned on the upper and lower models of the arches. The virtual attachments are designed to interoperate with the connection member 30 to slidably secure the attachments on the appliances when they are fabricated. Once positioned, a template is produced to allow the physical attachments 32 and 34 to be mounted on the appliances.

Once the data set for the desired teeth position with the proper bite occlusion has been created, the appliances may be fabricated as follows. The fabrication method employs a rapid prototyping device such as a stereolithography machine. A particularly suitable rapid prototyping machine is Model SLA-250/50 available from 3D System, Valencia, Calif. The rapid prototyping machine selectively hardens a liquid or other non-hardened resin into a three-dimensional structure which can be separated from the remaining non-hardened resin, washed, and used either directly as the appliance or indirectly as a mold for producing the appliance. The prototyping machine receives the individual digital data sets and produces one structure corresponding to each of the desired appliances. Generally, because the rapid prototyping machine may utilize a resin having non-optimum mechanical properties and which may not be generally acceptable for patient use, it will be preferred to use the prototyping machine to produce molds which are, in effect, positive tooth models of each successive stage of the treatment. After the positive models are prepared, a conventional pressure or vacuum molding machine may be used to produce the appliances from a more suitable material, such as 0.03 inch thermal forming dental material, available from Tru-Tain Plastics, Rochester, Minn. 55902. Suitable pressure molding equipment is available under the trade name BIO-STAR from Great Lakes Orthodontics, Ltd., Tonawanda, N.Y. 14150. The molding machine produces each of the appliances directly from the positive tooth model and the desired material. Suitable vacuum molding machines are available from Raintree Essix, Inc. After production, the plurality of appliances which comprise the system of the present invention are preferably supplied to the surgeon.

The appliance may be comprised of portions with differing elastic moduli. Elastic modulus may be used to express or describe the stiffness of a material or a material's resistance to elastic deformation. Therefore, elastic modulus may be used hereinafter to refer to stiffness. The elastic modulus of a material is the ratio of the increment of unit stress to an increment of unit deformation within the elastic limit. When a material is deformed within the elastic limit, the bonds between adjacent atoms are stretched but not broken. The magnitude of the elastic modulus is indicative of the atomic and molecular bonding forces. When the stress is relieved, the material returns to its original shape and the deformation is nonpermanent. Different materials may have different elastic moduli based on their molecular structures. Some materials, such as certain polymers, may be specially produced to have different elastic moduli while retaining similar chemical compositions (and thus assuring compatibility of the different modulus materials in a single structure). Likewise, the elastic modulus of a polymer or other material may be enhanced or otherwise modified. This may be achieved by adding a powder, such as $CaCO_3$, talc, $TiO_2$, glass, diamond or a polymer powder, to name a few. In addition, this may be achieved by embedding structural reinforcements, such as metal pieces, strips, wires, mesh, lattices, networks, polymeric filaments, or the like. In addition, the elastic modulus may be altered by post-production methods, such as layering, coating, interpenetrating, treating with various chemical agents, and altering the temperature, to name a few. In the resulting appliance, the elastic moduli of the varying portions will usually range from 0.5 to 5 GigaPascal (GPa), although in some instances portions of the appliance may fall outside of this range. The elastic modulus of one portion may differ from another portion by 25% to 600%, or more.

The differing elastic moduli of different portions of the dental appliance shells of the present invention will exist while the device is present over teeth in a normal oral environment. Thus, different portions of the appliance shell will impart different forces to the immediately underlying teeth, where the level of the force depends both on the device geometry or tooth positions (relative to the underlying tooth or teeth, which may vary over time) and on the elastic modulus of that portion of the device (which will remain constant over time in the normal oral environment). In one embodiment, portions of the shell of the elastic repositioning appliance may differ in elastic moduli along a mesial-distal axis. A mesial-distal axis may be defined as an axis following the gingival line or dental arch. Thus, the elastic repositioning appliance may be comprised of portions with a lower elastic modulus covering the molars, for example, and portions with a higher elastic modulus covering the remainder of the teeth. In this example, the portions may be relatively large so that a portion may receive one or more teeth, such as contiguous molars. This may be utilized when one or more teeth are to provide an anchor or base region for imparting repositioning force against another tooth or teeth. The portion of the appliance covering the anchor teeth may be of a relatively flexible nature with a lower elastic modulus than the portion covering the teeth to be repositioned. This is because the portions covering the anchor teeth may not need to apply repositioning forces to the teeth they cover; they may merely be designed to hold the appliance in place. Consequently, a high level of rigidity or stiffness may not be required. However, it may be appreciated that portions covering anchor teeth may in fact require a higher stiffness material than other portions, including portions which are designed to apply repositioning forces. Thus, any variation of stiffness or elastic modulus along a mesial-distal axis is included in this embodiment. The introduction of such portions or regions with more flexibility provides utility in ease of use for the patient. The patient may find ease in positioning the appliance with the more flexible portions first which may guide the appliance in placement of the more rigid, slightly misfit portions designed for repositioning. This sequence may be reversed in removal of the appliance. Likewise, such flexibility may also allow for any slight differences in mold versus appliance versus dentition geometry which may otherwise make placement and removal of the appliance more difficult. In some cases, a generally misfit appliance may "pop off" or have a tendency to disengage even when properly positioned over the teeth. Increased flexibility may reduce these tendencies.

In further embodiments, portions of the elastic repositioning appliance may vary in elastic moduli along different and/or additional axes. For example, moduli may vary along a facial-lingual axis. Facial may be defined as next to or toward the lips or cheek, including terms labial and buccal. Lingual may be defined as next to or toward the tongue. Thus, a facial-lingual axis may be described as an axis following a radial or similar line from the tongue toward the lips or cheek and vice versa. Likewise, moduli may vary along a gingival-crown axis. This may be described as a substantially vertical axis following a line from the top of the crown at the edge of the occlusal surface of a tooth toward the gingival line or root and vice versa. In a preferred embodiment, an appliance may have a portion with a lower elastic modulus covering the occlusal surfaces of the teeth and a portion with a higher elastic modulus covering the remaining surfaces of the teeth. Thus, the moduli may vary along a facial-lingual axis and/or a gingival-crown axis, depending on the boundaries of the delineated portions. Such a design may incorporate added flexibility to the appliance while maintaining adequate repositioning forces in the most efficient areas.

It may be appreciated that the elastic modulus of the appliance shells may vary over any number of delineated portions. Such portions may be of any size, shape, thickness, or dimension. Thus, such portions may receive entire teeth or they may be of the size to cover only a portion of a tooth or dental surface. When portions are relatively large, an appliance may be divided into, for example, two to five portions. Portions adjacent to one another differ in elastic moduli, however not all portions of an appliance may differ from each other, such as in the case of an appliance with portions alternating between two moduli. When portions are relatively small, an appliance may contain an unlimited number of portions, varying along any axis or combination of axes.

In another aspect, the elastic modulus of an appliance or portions of an appliance may be modified in a number of different ways. To begin with, the elastic modulus may be determined by the choice of materials. For example, metals will generally have a higher elastic modulus than polymers due to atomic structure. For example, the modulus values for metals may range between 48 and 414 GPa, whereas the modulus for polymers may range from 0.5 to 35 GPa. Thus, it will be possible to form appliances having moduli which differ greatly by forming different portions from metal(s) and polymer(s), or by forming successive appliances from metals and polymers. Usually, however, the appliances will comprise or consist of a polymeric shell formed from a single polymer, multiple polymers, copolymers, and the like, typically by thermoforming and/or lamination. Stiffness of a polymer may be varied within a range (typically 0.5 GPa to 5 GPa) by changing the molecular structure of the polymer chains. Polymer chains with hindered side-chains are unable to pack as closely as those with smaller side-chains. Thus, such a polymer may have more intermolecular motion and therefore a lower bulk elastic modulus. Stiffness can also be changed by controlling the degree of cross-linking as well as the cross-linking entity within a polymer or copolymer. Further, alternatively, differing elastic moduli may be created within the same polymer shell by layering or laminating the same or different polymers. Two layers of a polymer material bonded together may have a higher elastic modulus than a single layer of such material. Thirdly, different elastic moduli may be created with a single layer of one type of polymer material by production methods, such as coating, treating with various chemical agents, and altering the temperature, to name a few.

Further, different elastic moduli may be produced by forming selectively reinforced and/or composite-type materials. For example, a polymer material may be reinforced with structures such as strips, wires, pieces, mesh, lattices, networks, and the like. These structures may be comprised of any suitable material, particularly metals and alloys but also including polymer filaments, wires, braids, and the like. Likewise, composite materials may be comprised of interpenetrating polymeric networks. An interpenetrating polymeric network is comprised of a base material and an additional material that interpenetrates the base material to alter its mechanical properties. For example, the base material (A) may be a solid polycarbonate. The added material (B) may be a liquid polymer, monomer or cross linking agent which is allowed to interpenetrate and activate to form a composite network. The composite (A+B) may have a stiffness which is greater than the sum of its parts, (A) and (B). Further, another material (C) may also be allowed to interpenetrate and activate to form a new composite network. The composite (A+B+C) may also have a stiffness which is greater than the sum of its parts, (A), (B) and (C). With this method, any number of composites may be formed providing a wide range of mechanical properties, specifically stiffnesses. In addition, a number of these production methods may provide materials with gradual changes in elastic moduli. For example, purposely irregular coating of a polymer material may provide higher stiffness in areas with thicker coating and lower stiffness in areas with thinner coating. This may be applied to a number of production methods.

The appliance material may have physical properties for precise fitting over the teeth of the patient and should also be easily removable due to the post surgical fragile state of the patient. The appliance material may have environmental switching properties for changing physical properties for easy removal and insertion purposes. The removal mechanism may be an integral property or characteristic of the shell and/or may be a separate component or components in addition to the shell. Exemplary shell properties include changes in stiffness or shape induced by exposure of the shell to different environmental conditions, e.g. a change in temperature, a change in pH, a change in ionic strength, or the like. Exemplary additional components include adhesives, interface layers (between the shell and the tooth), tooth anchors, reinforcement components (layers, filaments, braids, etc.), where such components can change stiffness, dimensions, orientations, or the like to selectively hold or release the shell onto the teeth. Usually, the changes in the additional components will be induced by the same types of environmental changes used for inducing property changes in the shell. Alternatively, removal mechanisms comprising separate components could be stimulated by exposure to an external energy source, e.g. being mechanically, electrically, optically, magnetically or otherwise triggered to induce a change which causes or permits release of the shell from the teeth. Use of such removal mechanisms is advantageous in a number of respects. Environmental changes can be easily implanted by a practitioner or patient. For example, the practitioner or patient can wash the mouth with an appropriately heated, pH-modified, ionic strength controlled, or other solution which can induce the desired change in the removal mechanism. While the use of mechanically, electrically, or optically triggered removal mechanisms may require additional equipment, such mechanisms can also be very simple and suitable for use by the patient as well as the practitioner. In all cases, the removal mechanisms can usually be made reversible, i.e. the appliance can be "switchable" between attached configurations where the appliance will remain in place on the teeth and a release configuration where the appliance can be removed form the teeth. This is a particular advantage since is allows the appliance to be temporarily "reconfigured" and removed for any purpose and then repositioned over the teeth to continue the treatment.

In one embodiment, a state change reduces the stiffness or shape (or both) of the shell material such that the engagement forces between the shell and the teeth or other interfaces are reduced or eliminated. The state change can be a change in any material property which affects stiffness or shape, such as hardness/softness (as measured by durometer), elasticity, phase (as with shape memory polymers and materials), or the like. Preferably, the state change will be reversible so that the shell can recapture the stiffness lost or recover the shape which was lost while undergoing the initial state change. The reduction of stiffness will usually comprise a softening and/or increasing elasticity of the shell material, permitting the shell to become more easily pulled from over the teeth. A change in shape will reduce or eliminate engagement forces between the appliance and the teeth or other interfaces due to an expansion, contraction, partial opening, reduction of interference, or other reconfiguration of the appliance. The desired state change will preferably be induced by an environmental change which can easily be effected in the patient's mouth. Preferred environmental changes are these which can be implemented by a simple mouth wash with a solution having a particular composition, pH, temperature, ionic strength or other property. The selected property should be one that the patient will not normally encounter in daily life, at least during periods when release of the appliance is not intended. For example, temperature would not be a good choice unless it is intended that the appliance be removed when eating or drinking hot foods and drinks. The property should also be one that is physiologically acceptable, e.g. very high or very low pH might not be desirable.

It is not necessary, however, that the "released" configuration be long term or sustainable. In many instances, the removal mechanism will permit mounting of the appliance onto the teeth when the removal mechanism is in its "attached" configuration. To remove the appliance, the released configuration need be sustained only long enough to complete the removal. The removal mechanism can then revert to the attached configuration, as the result of for example, cooling, pH change, and ionic strength change, and still be replaced over the teeth without the need to restore the released configuration.

The removal mechanism may be an integral property of the appliance, usually being an inherent property of the shell or a part of the shell. An orthodontic appliance is provided which has a shell formed of at least one layer of a polymeric material. The shell has a cavity which fits closely over a contiguous group of teeth. A contiguous group of teeth includes at least 3 teeth, but usually 4 or more. The at least one-layer of polymeric material has a first state where the appliance is held onto the teeth and a second state where the appliance may be removed from the teeth. The first state will exist when the shell is in place in the patient's mouth in the absence of any "non-oral" conditions or externally applied energy or other stimuli. The second state can then be selectively induced by creating a "non-oral" environment in the patient's mouth, as discussed above. The non-oral environment may consist of a non-physiological temperature (above 37.degree. C., preferably 40-55.degree. C.; or below 37.degree. C., preferably below 30.degree. C. a non-physiologic pH (above 8, preferably above 9, more preferably above 8.5 or below 7, preferably below 6, more preferably below 6.5), a non-physiologic ionic strength, such as 3% sodium chloride, or the like.

In another embodiment, the removal mechanism is formed as one or more additional component(s) or mechanism(s). Such systems will include at least one polymeric shell which can be removably placed over a patient's teeth. The separate removal component or mechanism is switchable from a first state to a second state.

In yet another embodiment, a dental appliance system will include a dental appliance, which has a shell with a cavity. The system will further include an attachment device which is formed or exists separately from the shell. The attachment device is usually configured to be positioned between the outer surface of the teeth and an inner surface of the cavity. The device is switchable between a first state, where the appliance is held onto the teeth, and a second state, where the appliance may be removed from the teeth. The switch is stimulated or made to occur as a response to an environmental change.

In another aspect of the invention, an improved method is provided for removing an appliance from the teeth. Preferably, the appliance is a polymeric shell, which has cavities shaped to receive and resiliently reposition teeth to produce a final tooth arrangement. In a first aspect, the improvement comprises transforming the shell from a first state, where the appliance is held onto the teeth, to a second state where the appliance may be removed from the teeth. The transformation is performed in situ in the patient's mouth, usually the exposure to an environmental change or external stimulus as described above. The transformation is repeatable so that the appliance can be reinserted.

In another aspect a method for fabricating a removable incremental tooth position adjustment appliance is provided including forming a shell of at least one layer of a polymeric material with a teeth mold. The shell is formed with cavities shaped to receive and resiliently reposition teeth from one arrangement to a successive arrangement. The shell transforms from a first state, where the appliance is held onto the teeth, to a second state, where the appliance may be released from the teeth. The polymeric layers can be a material selected from the group consisting of memory polymers, methacrylate containing polymers, acrylate containing polymers, thermoplastic polymers, cross-linked thermoplastic polymers, thermoplastic polymer blends, cross-linked thermoplastic polymer blends, thermoplastic elastomer polymers, and thermoset polymers.

The appliance material may have the ability to carry active ingredients and release it in a controlled fashion. For example, such ingredients may include fluoride and/or any therapeutic compounds such as antibiotics or suitable medication. To enhance appearance, the appliance material may be transparent or having tooth matching color.

More information on the fabrication of the dental template or appliance is disclosed in U.S. Pat. No. 6,499,997 "Manipulable dental model system for fabrication of a dental appliance"; U.S. Pat. No. 6,497,574 "Modified tooth positioning appliances and methods and systems for their manufacture"; U.S. Pat. No. 6,488,499 "Methods for correcting deviations in preplanned tooth rearrangements"; U.S. Pat. No. 6,485,298 "System and method for releasing tooth positioning appliances"; U.S. Pat. No. 6,471,511 "Defining tooth-moving appliances computationally"; U.S. Pat. No. 6,463,344 "Efficient data representation of teeth model"; U.S. Pat. No. 6,457,972 "System for determining final position of teeth"; U.S. Pat. No. 6,454,565 "Systems and methods for varying elastic modulus appliances"; U.S. Pat. No. 6,450,807 "System and method for positioning teeth"; U.S. Pat. No. 6,409,504 "Manipulating a digital dentition model to form models of individual dentition components"; U.S. Pat. No. 6,406,292 "System for determining final position of teeth"; U.S. Pat. No. 6,398,548 "Method and system for incrementally moving teeth"; U.S. Pat. No. 6,394,801 "Manipulable dental model system for fabrication of dental appliances"; U.S. Pat. No. 6,390,812 "System and method for releasing tooth positioning appliances"; U.S. Pat. No. 6,386,878 "Systems and methods for removing gingiva from teeth"; U.S. Pat. No. 6,386,864 "Stress indicators for tooth positioning appliances"; U.S. Pat. No. 6,371,761 "Flexible plane for separating teeth models"; U.S. Pat. No. 6,318,994 "Tooth path treatment plan"; U.S. Pat. No. 6,309,215 "Attachment devices and method for a dental appliance"; U.S. Pat. No. 6,299,440 "System and method for producing tooth movement"; U.S. Pat. No. 6,227,851 "Manipulable dental model system for fabrication of a dental appliance"; U.S. Pat. No. 6,227,850 "Teeth viewing system"; U.S. Pat. No. 6,217,325 "Method and system for incrementally moving teeth"; U.S. Pat. No. 6,210,162 "Creating a positive mold of a patient's dentition for use in forming an orthodontic appliance"; and U.S. Pat. No. 5,975,893 "Method and system for incrementally moving teeth," the contents of which are hereby incorporated by reference.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A dental splint, comprising:
   upper and lower polymeric shell appliances having cavities shaped to receive and hold teeth on a patient's maxillary and mandibular arches, respectively, said upper and lower polymeric shell appliances comprising a plurality of delineated portions, at least one of said plurality of delineated portions having an elastic modulus that is different from at least another of said plurality of delineated portions;
   at least one connection member adapted to fixedly secure the upper and lower appliances together to prevent any significant movement of the arches relative to one another; and
   at least one upper portion protruding from the upper appliance and at least one lower portion protruding from the lower appliance, wherein the upper portion and lower portion are adapted to engage the connection member;
   wherein the connection member and the upper and lower portions comprise a pawl and ratchet system.

2. The dental splint of claim 1, wherein each appliance further comprises an appliance material with a first state for wearing the appliance and a second state for removing the appliance.

3. The dental splint of claim 1, wherein each appliance further comprises an appliance material carrying an active ingredient for intra-oral release.

4. The dental splint of claim 3, wherein the active ingredients may be fluoride and/or any therapeutic compounds.

5. The dental splint of claim 1, wherein each appliance further comprises an appliance material having either a transparent color or a tooth matching color.

6. A dental splint, comprising:
   upper and lower polymeric shell appliances having cavities shaped to receive and hold teeth on a patient's maxillary and mandibular arches, respectively, said upper and lower polymeric shell appliances comprising a plurality of delineated portions, at least one of said plurality of delineated portions having an elastic modulus that is different from at least another of said plurality of delineated portions;
   at least one connection member adapted to fixedly secure the upper and lower appliances together to prevent any significant movement of the arches relative to one another; and
   at least one upper portion protruding from the upper appliance and at least one lower portion protruding from the lower appliance, wherein the upper portion and lower portion are adapted to engage the connection member;
   wherein the connection member comprises a ladder adapted to engage the upper and lower portions.

7. The dental splint of claim 6, wherein each appliance further comprises an appliance material with a first state for wearing the appliance and a second state for removing the appliance.

8. The dental splint of claim 6, wherein each appliance further comprises an appliance material carrying an active ingredient for intra-oral release.

9. The dental splint of claim 8, wherein the active ingredients may be fluoride and/or any therapeutic compounds.

10. The dental splint of claim 6, wherein each appliance further comprises an appliance material having either a transparent color or a tooth matching color.

11. A dental splint, comprising:
upper and lower polymeric shell appliances having cavities shaped to receive and hold teeth on a patient's maxillary and mandibular arches, respectively, said upper and lower polymeric shell appliances comprising a plurality of delineated portions, at least one of said plurality of delineated portions having an elastic modulus that is different from at least another of said plurality of delineated portions;
at least one connection member adapted to fixedly secure the upper and lower appliances together to prevent any significant movement of the arches relative to one another; and
at least one upper portion protruding from the upper appliance and at least one lower portion protruding from the lower appliance, wherein the upper portion and lower portion are adapted to engage the connection member;
wherein the connection member comprises a bead string adapted to engage the upper and lower portions.

12. The dental splint of claim 11, wherein each appliance further comprises an appliance material with a first state for wearing the appliance and a second state for removing the appliance.

13. The dental splint of claim 11, wherein each appliance further comprises an appliance material carrying an active ingredient for intra-oral release.

14. The dental splint of claim 13, wherein the active ingredients may be fluoride and/or any therapeutic compounds.

15. The dental splint of claim 11, wherein each appliance further comprises an appliance material having either a transparent color or a tooth matching color.

16. A dental splint, comprising:
upper and lower polymeric shell appliances having cavities shaped to receive and hold teeth on a patient's maxillary and mandibular arches, respectively, said upper and lower polymeric shell appliances comprising a plurality of delineated portions, at least one of said plurality of delineated portions having an elastic modulus that is different from at least another of said plurality of delineated portions;
at least one connection member adapted to fixedly secure the upper and lower appliances together to prevent any significant movement of the arches relative to one another; and
at least one upper portion protruding from the upper appliance and at least one lower portion protruding from the lower appliance, wherein the upper portion and lower portion are adapted to engage the connection member;
wherein the connection member comprises a hasp.

17. The dental splint of claim 16, wherein the hasp snaps onto the upper and lower portions to prevent significant relative motion between the upper and lower appliances.

18. The dental splint of claim 16, wherein one of the upper and lower portions further comprises a hook.

19. The dental splint of claim 16, wherein each appliance further comprises an appliance material with a first state for wearing the appliance and a second state for removing the appliance.

20. The dental splint of claim 16, wherein each appliance further comprises an appliance material carrying an active ingredient for intra-oral release.

21. The dental splint of claim 20, wherein the active ingredients may be fluoride and/or any therapeutic compounds.

22. The dental splint of claim 16, wherein each appliance further comprises an appliance material having either a transparent color or a tooth matching color.

23. A dental splint, comprising:
upper and lower polymeric shell appliances having cavities shaped to receive and hold teeth on a patient's maxillary and mandibular arches, respectively, said upper and lower polymeric shell appliances comprising a plurality of delineated portions, at least one of said plurality of delineated portions having an elastic modulus that is different from at least another of said plurality of delineated portions;
at least one connection member adapted to fixedly secure the upper and lower appliances together to prevent any significant movement of the arches relative to one another; and
at least one upper portion protruding from the upper appliance and at least one lower portion protruding from the lower appliance, wherein the upper portion and lower portion are adapted to engage the connection member;
wherein the connection member comprises a clip adapted to slidably engage the upper and lower portions.

24. The dental splint of claim 23, wherein each appliance further comprises an appliance material with a first state for wearing the appliance and a second state for removing the appliance.

25. The dental splint of claim 23, wherein each appliance further comprises an appliance material carrying an active ingredient for intra-oral release.

26. The dental splint of claim 25, wherein the active ingredients may be fluoride and/or any therapeutic compounds.

27. The dental splint of claim 23, wherein each appliance further comprises an appliance material having either a transparent color or a tooth matching color.

* * * * *